United States Patent
Auerbach et al.

(10) Patent No.: US 11,576,603 B2
(45) Date of Patent: Feb. 14, 2023

(54) COMPRESSED-SENSING OF SPATIOTEMPORALLY-CORRELATED AND/OR RAKENESS-PROCESSED ELECTROGRAMS

(71) Applicants: Biosense Webster (Israel) Ltd., Yokneam (IL); Stichting voor de Technische Wetenschappen, Ulrecht (NL); Technische Universiteit Delft, Delft (NL)

(72) Inventors: Shmuel Auerbach, Kerem Maharal (IL); Wouter A Serdijn, Delft (NL); Samprajani Rout, Delft (NL)

(73) Assignee: Biosense Webster (Israel) Ltd., Yokneam (IL)

( * ) Notice: Subject to any disclaimer, the term of this patent is extended or adjusted under 35 U.S.C. 154(b) by 291 days.

(21) Appl. No.: 16/846,551

(22) Filed: Apr. 13, 2020

(65) Prior Publication Data
US 2020/0337579 A1  Oct. 29, 2020

Related U.S. Application Data

(60) Provisional application No. 62/838,489, filed on Apr. 25, 2019.

(51) Int. Cl.
*A61B 5/316* (2021.01)
*A61B 5/00* (2006.01)
(Continued)

(52) U.S. Cl.
CPC ............ *A61B 5/316* (2021.01); *A61B 5/0006* (2013.01); *A61B 5/30* (2021.01); *A61B 5/369* (2021.01); *A61B 5/6801* (2013.01)

(58) Field of Classification Search
CPC ......... A61B 5/0006; A61B 5/30; A61B 5/316; A61B 5/369; A61B 5/6801; H03M 7/3062; H03M 7/3068
(Continued)

(56) References Cited

U.S. PATENT DOCUMENTS 8,456,182 B2   6/2013  Bat-Tal et al.
2005/0055060 A1*  3/2005  Koh .................... A61N 1/365
                                                         607/17
(Continued)

OTHER PUBLICATIONS

Singh et al., "Weighted mixed-norm minimization based joint compressed sensing recovery of multi-channel electrocardiogram signals", Computers and Electrical Engineering, 53: pp. 203-218 (Year: 2016).*

(Continued)

*Primary Examiner* — Jonathan T Kuo
*Assistant Examiner* — Vynn V Huh
(74) *Attorney, Agent, or Firm* — Dergosits & Noah LLP; Todd A. Noah

(57) ABSTRACT

An apparatus includes data acquisition circuitry and a processor. The data acquisition circuitry is configured to acquire multiple signals using multiple respective electrodes of an array of electrodes coupled to one of an organ of a patient and tissue or a cell culture. The processor is configured to hold a definition of a mixed-norm that is defined as a function of relative positions of the electrodes in the array, and jointly compress the multiple signals in a compressed-sensing (CS) process that minimizes the mixed-norm.

21 Claims, 7 Drawing Sheets

(51) Int. Cl.
    *A61B 5/30*     (2021.01)
    *A61B 5/369*     (2021.01)
    *H03M 7/30*     (2006.01)

(58) Field of Classification Search
    USPC .................. 600/16–18, 300–301, 508–528
    See application file for complete search history.

(56) References Cited

U.S. PATENT DOCUMENTS

| | | | |
|---|---|---|---|
| 2015/0036021 A1* | 2/2015 | Gigan | G02B 5/0273 348/231.6 |
| 2016/0278713 A1* | 9/2016 | Shoaran | A61B 5/7232 |

OTHER PUBLICATIONS

European Search Report for corresponding EPA No. 20171243.7 dated Sep. 22, 2020.

Singh, Anurag et al., "Weighted mixed-norm minimization based joint compressed sensing recovery of multi-channel electrocardiogram signals", Computers & Electrical Engineering, vol. 53, pp. 203-218 Feb. 19, 2016.

Singh, Anurag et al., "Block sparsity-based joint compressed sensing recovery of multi-channel ECG signals", Healthcare Technology Letters, vol. 4, No. 2, pp. 50-56, May 1, 2017.

Candas, Emmanuel J. et al., "Enhancing Sparsity by Reweighted l1 Minimization", Journal of Fourier Analysis and Applications, vol. 14, No. 5-6, pp. 877-905, Oct. 15, 2008.

"Rakeness in the Design of Analog-to-Information Conversion of Sparse and Localized Signals," by M. Mangia et al., IEEE Transactions on Circuits and Systems—I: Regular Papers, vol. 59, No. 5, May 2012.

* cited by examiner ated and rakeness-pro- cessed compressed sensing (CS) of electrograms, in accor- dance with an embodiment of the present invention;

COMPRESSED-SENSING OF SPATIOTEMPORALLY-CORRELATED AND/OR RAKENESS-PROCESSED ELECTROGRAMS

CROSS-REFERENCE TO RELATED APPLICATIONS

This application claims the benefit of U.S. Provisional Patent Application 62/838,489, filed Apr. 25, 2019, whose disclosure is incorporated herein by reference.

FIELD OF THE INVENTION

The present invention relates generally to processing and communicating patient health data, and particularly to electrophysiological data compression.

BACKGROUND OF THE INVENTION

Various known methods were proposed to facilitate remote diagnosis of medical conditions, such as heart problems. For example, South Korean Patent KR 101526774 describes an electrocardiogram sensing apparatus comprising: (a) an electrocardiogram sensing unit for measuring a user's electrocardiogram signal; a processor for filtering the measured electrocardiogram signal using a bandpass filter and for compressing and sensing the filtered electrocardiogram signal; and a data communication unit for transmitting the compressed sensed electrocardiogram signal to the electrocardiogram monitoring device; (b) a first communication unit for receiving the compression sensed electrocardiogram signal; a processor for restoring the compressively sensed electrocardiogram signal and analyzing the restored electrocardiogram signal; and a display unit for outputting the electrocardiogram analysis data; and (c) an electrocardiogram monitoring apparatus.

SUMMARY OF THE INVENTION

An embodiment of the present invention that is described hereinafter provides an apparatus including data acquisition circuitry and a processor. The data acquisition circuitry is configured to acquire multiple signals using multiple respective electrodes of an array of electrodes coupled to one of an organ of a patient and tissue or a cell culture. The processor is configured to hold a definition of a mixed-norm that is defined as a function of relative positions of the electrodes in the array, and jointly compress the multiple signals in a compressed-sensing (CS) process that minimizes the mixed-norm.

In some embodiments, the signals are one of atrial electrograms and ventricular electrograms. In other embodiments, the signals are electroencephalograms.

In some embodiments, the data acquisition circuitry is further configured to apply respective pseudo-random sequences to the signals so as to increase sparsity and incoherence of a measurement matrix $\Phi$, and wherein the processor is configured to minimize the mixed-norm for the measurement matrix $\Phi$ having the increased sparsity and incoherence.

In an embodiment, the data acquisition circuitry includes a pseudo-random binary noise (PRBS) generator for generating the pseudo-random sequences. In another embodiment, the data acquisition circuitry includes a Walsh-Hadamard orthogonal coding (WHOC) generator for generating the pseudo-random sequences.

In some embodiments, the data acquisition circuitry is further configured to spectrally spread the input signal.

In some embodiments, the data acquisition circuitry includes a single analog-to-digital convertor (ADC) configured to convert the multiple signals into digital signals.

In an embodiment, the apparatus further includes a wireless unit configured to transmit the compressed signals to a base station.

In another embodiment, the apparatus further includes a wearable package containing the data acquisition circuitry and the processor.

There is additionally provided, in accordance with another embodiment of the present invention, an apparatus including data acquisition circuitry and a processor. The data acquisition circuitry is configured to acquire multiple signals using multiple respective electrodes of an array of electrodes coupled to one of an organ of a patient and tissue or a cell culture, wherein the data acquisition circuitry includes a pseudo-random bit sequence generator and a modulator, the pseudo-random bit sequence generator configured to drive the modulator, thereby simultaneously acquiring the signals and suppressing flicker noise of a front-end of the signal acquisition circuitry. The processor is configured to hold a definition of a mixed-norm that is defined as a function of relative positions of the electrodes in the array, jointly compress the multiple signals in a spatial domain and in a time domain, and reconstruct the multiple signals using the mixed-norm in a recovery algorithm which takes into account signals energies.

There is further provided, in accordance with another embodiment of the present invention, a method including acquiring multiple signals using multiple respective electrodes of an array of electrodes coupled to one of an organ of a patient and tissue or a cell culture. A definition of a mixed-norm is held, that is defined as a function of relative positions of the electrodes in the array. The multiple signals are jointly compressed in a compressed-sensing (CS) process that minimizes the mixed-norm.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
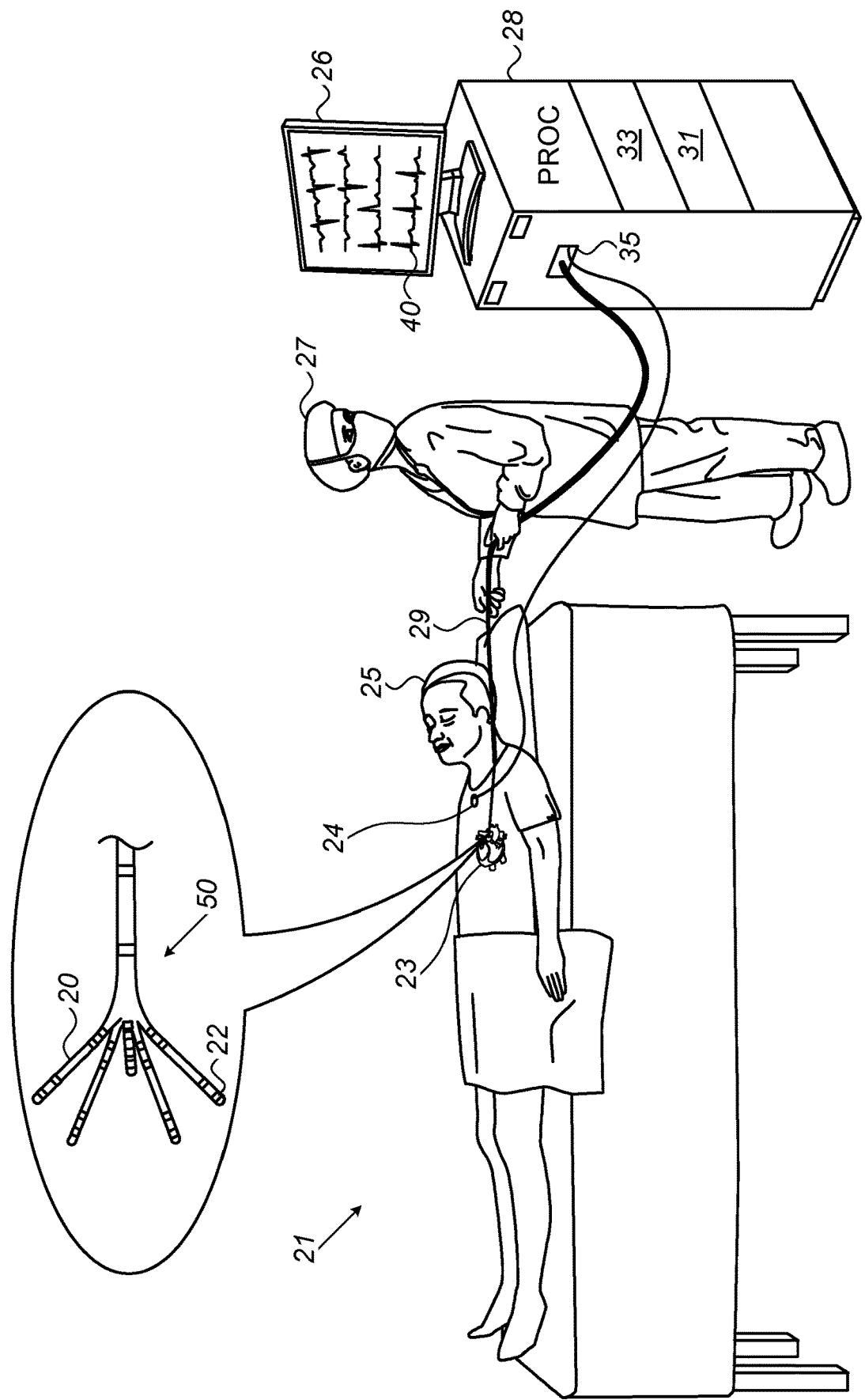
FIG. 1 is a schematic, pictorial illustration of a system for electrophysiological (EP) mapping, in accordance with an exemplary embodiment of the present invention.

Some electrophysiological (EP) disorders, such as cardiac arrhythmia and epileptic seizures, may be manifested in occasional episodes of rapidly varying EP signals, such as electrograms or electroencephalograms, respectively, which may appear irregular. Early detection and characterization of such cardiac or brain disorders is not straightforward and poses difficulties to the clinician.

Acquiring analog EP signals (also called hereinafter "waveforms") with a high spatiotemporal resolution, either invasively (e.g., using an implant or a catheter to acquire atrial electrograms), or using electrodes attached to skin (e.g., to acquire electroencephalograms), are a promising approach for early detection of such disorders.

For example, to detect cardiac arrhythmia, e.g., atrial fibrillation (AF), electrograms of diagnostic value may be acquired by a dense multi-electrode array (e.g., an implanted electrode array), normally for time periods ranging from 30 seconds to several minutes. However, this generates extremely large quantities of raw multi-channel data that are difficult to manage, record, and wirelessly transmit, in particular by low-power devices, such as a wearable unit coupled to an implanted electrode array.

Moreover, the high data rates required for transmitting electrograms/electroencephalograms (e.g., from a wearable acquisition module connected to an electrode array implant to a base station) are expensive in terms of power consumption and resources, making the use of an implant or a wearable module for early diagnosis of some arrhythmias impractical.

While existing methods of data compression may assist in reducing data volumes of regular EP signals, such as of sinus rhythms, electrogram signals that are irregular during arrhythmia cannot be sufficiently compressed with such methods, and, by the nature of arrhythmia, there is no way of knowing whether data compression of chaotic electrogram signals is sufficiently accurate, which may lead to loss of vulnerable data.

Compressed sensing (CS) is a promising approach to achieve data compression of EP signals, such as occurring during arrhythmia or epileptic seizure. In essence, CS is a linear programming optimization problem that attempts to span a waveform (i.e., the analog signal) with a minimal number of base-functions, below the Nyquist rate of the waveform. The spanning, which is approximate, is done by iteratively approximating a solution for a linear system of equations, by minimizing a norm. The approach requires individual waveforms to be sparse. The approach further requires incoherence between a sensing matrix $\Phi$ and a representation matrix $\Psi$ made of a linear basis of vectors in which the signal is sparse. The "restricted isometry property" (RIP) characterizes the sensing matrix which is nearly orthonormal while operating on sparse vectors. A widely used norm in CS is the $\ell$ norm, defined below.

Some exemplary embodiments of the present invention that are described hereinafter use the high spatiotemporal correlation at which the electrograms are acquired (e.g., with some form of sufficiently dense electrode array), to perform compressed sensing (CS) of the multiple-electrogram data with a higher compression ratio (CR) than is possible by standard CS methods.

The high spatiotemporal correlation enables spanning (e.g., representing) waveforms (e.g., electrograms) at a same accuracy using fewer base-functions than with standard CS methods. At least some of the electrograms, e.g., the spatiotemporally correlated ones, require fewer base-functions to span by minimizing a mixed-norm $\ell_{1,2}$, defined below, which is built using the aforementioned spatiotemporal correlations.

In particular, knowing electrode array geometry, i.e., the positions of the sensing electrodes of the array relative to one another, enables the use of spatiotemporal correlations in the multi-channel electrograms to better CS the signals. In particular, using CS of the spatiotemporally-correlated signals, enables significant compression of the multi-channel electrograms without impacting the quality of data reconstructed from the compressed data (e.g., an SNR of the reconstructed data), and the clinical ability to use the data for diagnostic purposes.

In particular, using the disclosed mixed-norm $\ell_{1,2}$ yields higher CR per given (e.g., predefined) SNR, or same CR with higher SNR, than achievable using the widely used in CS $\ell_1$ norm.

In an exemplary embodiment, an apparatus is provided, that includes data acquisition circuitry and a processor. The data acquisition circuitry is configured to acquire multiple signals using multiple respective electrodes of an array of electrodes coupled to an organ of a patient. The processor is configured to (a) hold a definition of a mixed-norm, such as mixed-norm $\ell_{1,2}$, that is defined as a function of relative positions of the electrodes in the array, and (b) jointly compress the multiple signals in a compressed-sensing (CS) process that minimizes the mixed-norm.

Additionally, or alternatively to the above spatiotemporal property, in other exemplary embodiments, electrograms can be CS using a method called "rakeness." In the rakeness CS method, each electrogram is preprocessed by multiplying it with a pseudo-random code, comprising a time-sequence of "1", "0", and "−1". The operation of rakeness improves compression as follows: applying rakeness exploits the energy distribution in the waveform to increase a correlation of the electrogram waveform with a pseudo-random code configured to have the temporal statistics of the analog signal (i.e., correlated with a matrix comprising of {−1, 0, +1} values with similar statistical distribution as the electrogram waveform). The latter property is also called the aforementioned "restricted isometry property (RIP)," or "incoherence." This property enables to solve the electrogram waveform representation problem "accurately enough" with fewer base-functions than required without rakeness, and thus allows increasing CR while maintaining SNR. "Accurately enough" in CS usually means both in the $\ell_1$ norm and the mixed-norm $\ell_{1,2}$ minimization sense.

When using rakeness, the pseudo-random code and the input electrogram have similar energy spectra, and thus can capitalize on the temporal correlation that exists between them. Rakeness requires, and takes advantage of, sparsity of the multi-channel electrogram signals in both the spatial domain and the time domain.

In an exemplary embodiment, the aforementioned data acquisition circuitry is further configured to apply respective pseudo-random sequences to the signals so as to increase sparsity of the signals (a sparsity linear space is spanned by a basis in which the signal is sparse. In that basis, representation matrix $\Psi$ represents a "symlet" discrete wavelet transform), and wherein the processor is configured to minimize the mixed-norm for the signals having the increased sparsity and incoherence.

In another exemplary embodiment, the data acquisition circuitry comprises a single analog-to-digital convertor (ADC) configured to convert the multiple signals into digital signals, after rakeness was incorporated to each of these and, subsequently, the signals were multiplexed.

By utilizing spatiotemporally-correlated electrograms and/or rakeness-processed electrograms, a signal compressed by compressed sensing can be reconstructed with a better SNR, which allows for either a higher CR (enabling, for example, reduction of the required mobile transmission bandwidth), or for a better SNR for a given CR, compared with using conventional compressed sensing methods.

In some exemplary embodiments, an acquisition circuitry is provided to perform the rakeness using, for example, a pseudo-random binary sequence (PRBS) generator to provide the "1", "0", and "−1" sequenced signals. As noted above, rakeness-based CS allows for higher data rates to be transmitted (e.g., wirelessly) using low-power electronic resources, making such circuitries suitable, for example, for an implantable-wearable combo device, or for remote bandwidth-limited communication links (e.g., bandwidth-limited cellular links).

Moreover, more efficient decoding circuitry can be provided, e.g., inside a remote wireless device, to decompress the data (e.g., reconstruct the compressed data), and therefore, regardless of the acquisition technique (e.g., implant or catheter, local wireless or wired transmission), the compressed-sensing data can be wirelessly transferred to reconstruction in the remote wireless devices (e.g., a tablet with a cellular communication capability), for remote diagnosis.

In an exemplary embodiment, the aforementioned apparatus further comprises a wireless unit configured to transmit the compressed signals to a base station. In another embodiment, the apparatus further comprises a wearable package containing the data acquisition circuitry and the processor.

In some exemplary embodiments, the measurement matrix comprising of $\{-1, 0, +1\}$ values, which represents essentially a modulation operation, is used in order to suppress "1/f" acquisition noise and offset. The suppression of the 1/f noise and offset further reduces requirements from the acquisition circuitry and makes its miniaturization more feasible, e.g., for use in an implant or a wearable device.

Exemplary embodiments of the present invention pertain to using various forms and types of electrode arrays, such as those disposed on catheters, including, for example, basket, Pentaray™, multi-finger or multi-spline arrays such as a Picasso™ design, and any high-density grid array of known inter-electrode distances.

By providing highly efficient compressed sensing and reconstruction methods of arrhythmogenic signals, practical early-detection arrhythmia or epileptic-seizure monitoring devices may become available, and, furthermore, remote diagnosis may become more readily at hand. The present invention is particularly applicable for disease states in the electrophysiology field such as atrial fibrillation and ventricular fibrillation through the use of the aforementioned novel systems, methods, and algorithms to facilitate EP signal processing, planning, and diagnosis.

SYSTEM DESCRIPTION

Figure 2:
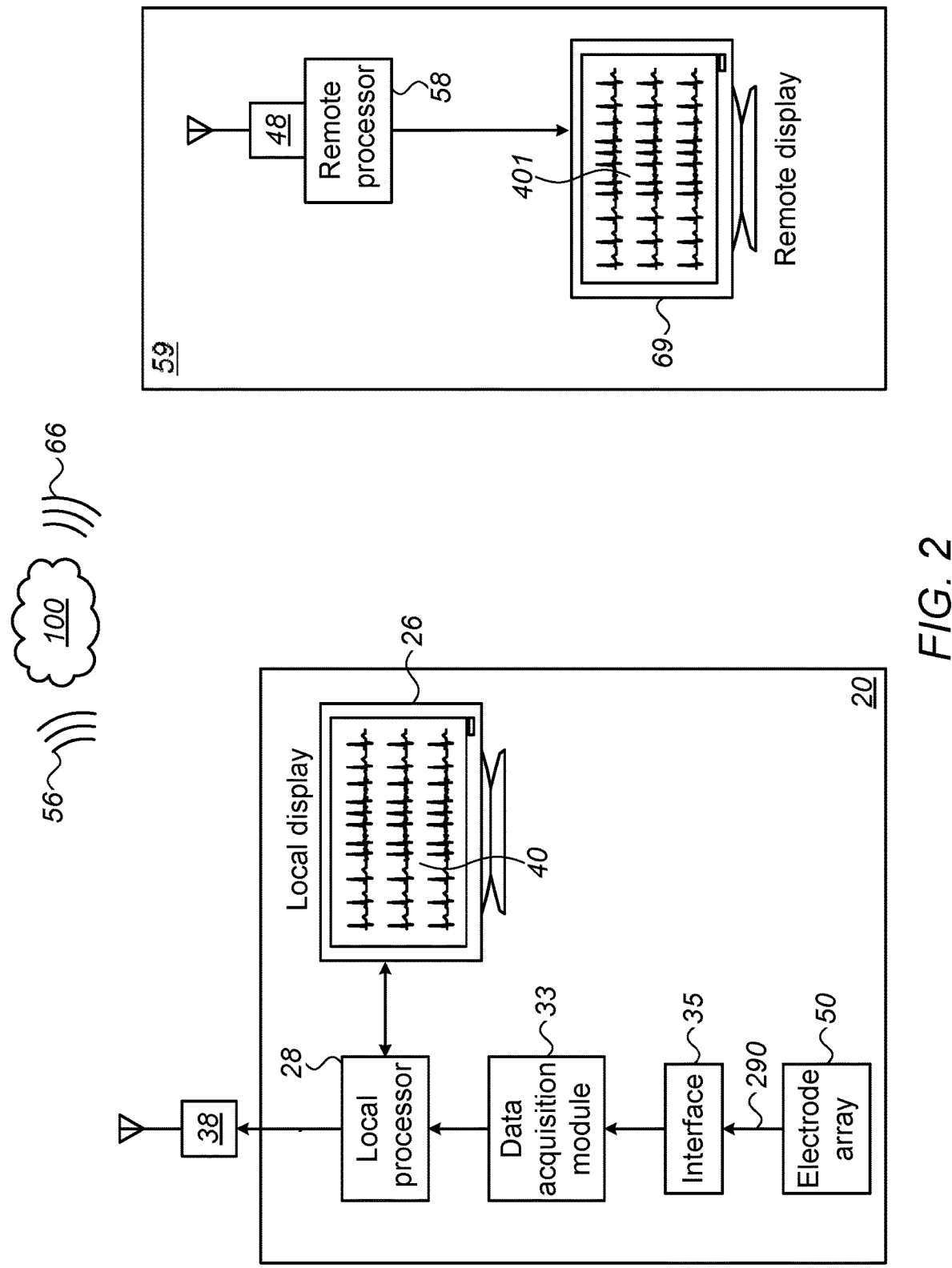
FIG. 2 is a block diagram that schematically illustrates a workflow in which electrograms are acquired and undergo compressed sensing (CS) by the system of FIG. 1, and afterwards remotely communicated and reconstructed, in accordance with an exemplary embodiment of the present invention.

As noted above, different types of medical devices, e.g., implants or catheters, may be used to invasively acquire multi-channel electrogram data with high spatiotemporal resolution. FIGS. 1 and 2 describe CS of catheter-acquired electrograms, whereas FIG. 3 describes CS of an implant-wearable combo device acquired electrograms. The two exemplary embodiments differ mainly in their different communication bottlenecks and power constraints that are overcome by the disclosed spatiotemporally correlated and rakeness-processed compressed sensing methods.

For example, with a catheterization system shown in FIG. 1, local acquisition and communication resources may be large enough and the compressed sensing be more critical for the remotely transmission, downloading and decoding of the medical data, as shown in FIG. 2. With the implant-wearable combo device shown in FIG. 3, local acquisition and communication resources are typically highly limited in the lightweight and small size combo device, and the disclosed methods are initially applied to solve these particular limitations.

FIG. 1 is a schematic, pictorial illustration of a system 21 for electrophysiological (EP) mapping, in accordance with an exemplary embodiment of the present invention. FIG. 1 depicts a physician 27 using an EP mapping catheter 29 to perform an EP mapping of a heart 23 of a patient 25. Catheter 29 comprises, at its distal end, a multi-channel electrode array 50 comprising one or more arms 20, each of which coupled to mapping-electrodes 22. During the mapping procedure, electrodes 22 acquire and/or inject signals from and/or to the tissue of heart 23. In particular, electrodes 22 acquire intra-cardiac EP signals, such as atrial electrograms (AEG).

The respective locations of mapping-electrodes 22 inside heart 23 (i.e., where the intra-cardiac ECG signals are measured) are tracked as well, so that the processor may link each acquired electrogram with the location at which the signal was acquired. System 20 externally senses electrical position signals and EP data, such as electrograms (ECG), using a plurality of external electrodes 24 coupled to the body of patient 25; for example, three external electrodes 24 may be coupled to the patient's chest, and another three external electrodes may be coupled to the patient's back. For ease of illustration, only one external electrode is shown in FIG. 1.

An example of a system capable of using the sensed electrical position signals to track the locations of mapping-electrodes 22 inside heart 23 of the patient is the CARTO® 3 system (produced by Biosense Webster, Irvine, Calif.). The CARTO® 3 system uses a tracking method named Advanced Current Location (ACL), which is described in detail in U.S. Pat. No. 8,456,182 whose disclosure is incorporated herein by reference.

A data acquisition module 33 receives the multiple electrogram signals conveyed to an electrical interface 35 over a wire link that runs in catheter 29. Using the sensed positions to establish spatiotemporal correlations between electrograms, and using the aforementioned rakeness method, a processor 28 performs compressed sensing on the AEG data contained in these signals. Processor 28 stores the compressed sensing electrograms in a memory 31, and later the CS signals are wirelessly communicated to a remote site (as shown in FIG. 2). In parallel, processor 28 may present the electrogram traces 40 on a display 26 of system 20.

The exemplary illustration shown in FIG. 1 is chosen purely for the sake of conceptual clarity. Other types of multi-electrode sensing geometries, such as of the Lasso® catheter (produced by Biosense Webster) may also be employed. Additionally, contact sensors may be fitted at the distal end of electro-anatomical catheter 29 and transmit data indicative of the physical quality of electrode contact with tissue. In an exemplary embodiment, measurements of some electrodes 22 may be discarded because their physical contact quality is poor, and the measurements of other electrodes may be regarded as valid because their contact quality is high.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm that enables processor 28 to perform the steps described in FIG. 4.

While the exemplary embodiment shown in FIG. 1 shows the processor used for CS external to module 33, in other embodiments, module 33 has its own processor to perform compressed sensing on the spatiotemporally correlated and/or rakeness-processed electrograms.

FIG. 2 is a block diagram that schematically illustrates a workflow in which electrograms are acquired and undergo compressed sensing (CS) by system 20 of FIG. 1, and afterwards remotely communicated and reconstructed, in accordance with an exemplary embodiment of the present invention.

As seen, the multiple electrogram data is locally communicated using a wire link 290 (e.g., that runs inside catheter 29) and (local) processor 28 performs compressed sensing on the spatiotemporally-correlated and/or rakeness-processed data. Physician 27 may inspect the data graphically on local display 26, for example, to evaluate a clinical relevance of the data.

In the illustrated exemplary embodiment, processor 28 is connected to a network 100 by a network interface, such as a network interface card (NIC) 38, and a link 56, which it uses to transmit the compressed sensing electrogram traces to a remote wireless device (e.g., a tablet) 59.

Compressed data may be first uploaded to a network 100 with link 56 supporting, for example, an upload rate of several megabit/sec, nowadays considered a limited rate. In an exemplary embodiment, wireless device 59 is bidirectionally connected to network 100 via an NIC 48 and a link 66. Wireless device 59 receives the compressed sensing electrogram traces and decompresses them using its processor 58 that furthermore presents the decompressed data on its display 69 (e.g., a tablet display). A medical expert may view the ECG traces 401 on display 69 and provide diagnosis from a distant location having limited access to communications (e.g., cellular only).

Figure 3:
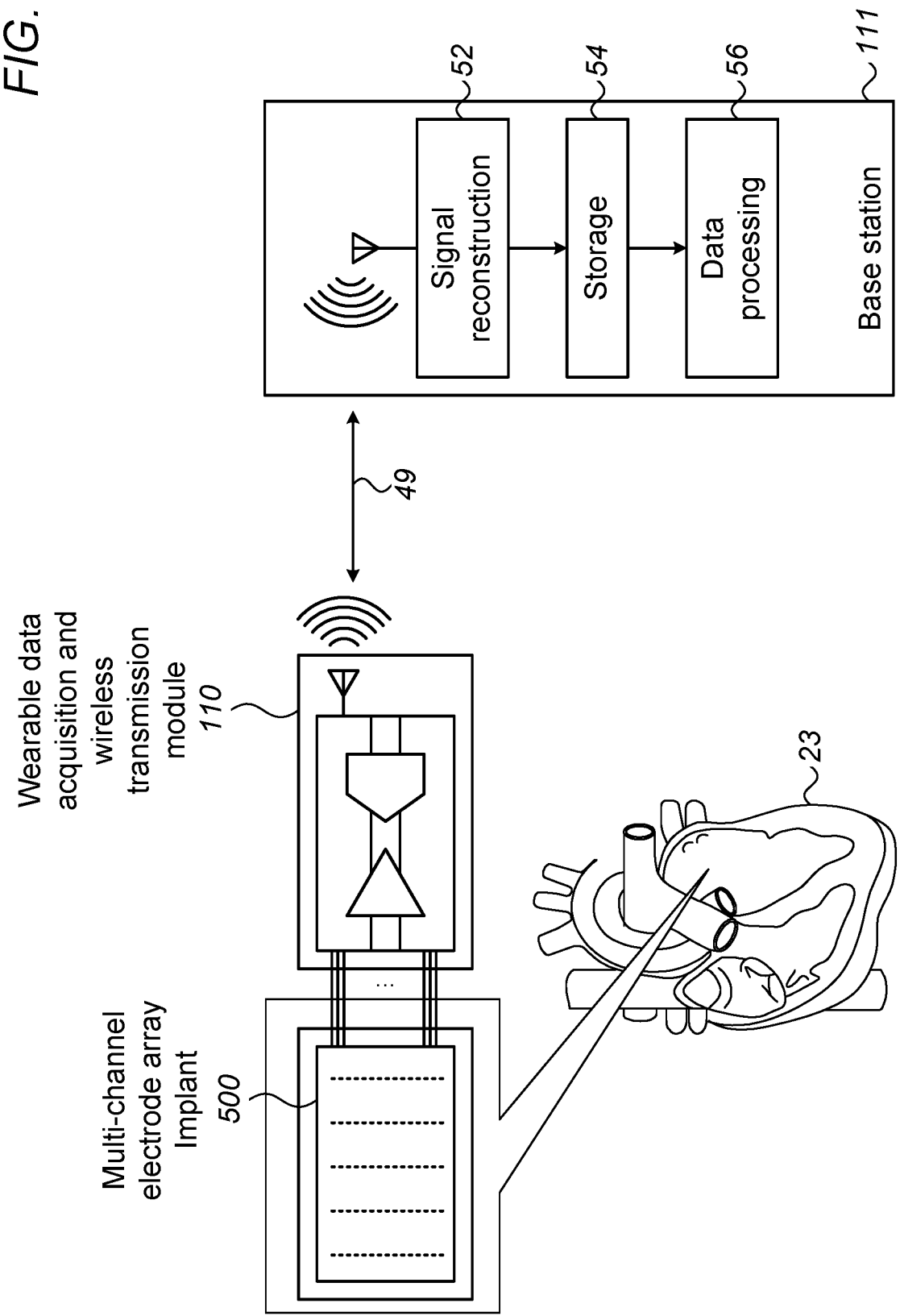
FIG. 3 is a schematic system-level diagram with a flow chart of an implanted-wearable combo device for compressed sensing (CS) and wireless transmission of electrograms, and of a base station receiving the CS electrograms, in accordance with another exemplary embodiment of the present invention.

FIG. 3 is a schematic system-level diagram with a flow chart of an implanted-wearable combo device 500/110 for compressed sensing (CS) and wireless transmission of electrograms, and of a base station 111 receiving the CS electrograms, in accordance with another exemplary embodiment of the present invention. As seen, a multi-channel electrode array implant 500 is located at a left atrium of heart 23. The array is connected by wires to a wearable data acquisition and wireless transmission module 110, which communicates with a base station 111 over a communication link 49.

Module 110 includes circuitry and a processor that enables the module to efficiently perform compressed sensing on the electrograms acquired by electrode array implant 500, utilizing spatiotemporally-correlated electrograms and/or rakeness-processed electrograms. Despite module 110's limited power source (e.g., a battery), the module is capable of acquiring and transmitting the AEG data at acceptable rates to a base station 111 by using the disclosed CS techniques.

For example, using an electrode array with an inter-electrode distance of 2 mm to acquire signals, electrograms from at least 1728 recording sites have to be CS, to cover an entire atrium, including the right atrium, the left atrium, and the Bachmann bundle. To record the signals from 1728 electrodes at a resolution of 16 bits and a sampling frequency of 10 kHz, the total data rate required is 16×10×1000×1728, or 276 Mbit/s, resulting in ≈16.6 Gbit/min. Restricting recording sites to a left atrium still results in a several Gbit/min data rate (i.e., on the order of 100 Mbit/sec).

The disclosed CS technique has to provide high CR, e.g., a CR above 4, to enable using remote devices with bandwidth-limited communication links. The high CR is further important to save battery power so such devices are available for patients to wear. A CR for digital signals can be estimated as a ratio of number of samples multiplied by number of bits. Therefore, a CR value of, e.g., 4, can be achieved by compressing the number of samples, e.g., from 512 to 256, and the number of bits, e.g., from 16 to 8.

In FIG. 3, base station 111 has the compressed sensing data downloaded using a wireless receiver, and the signal is consequently reconstructed (52), stored (54), and further processed (56), for example, for logging, visual presentation, and user alerts.

Figure 4:
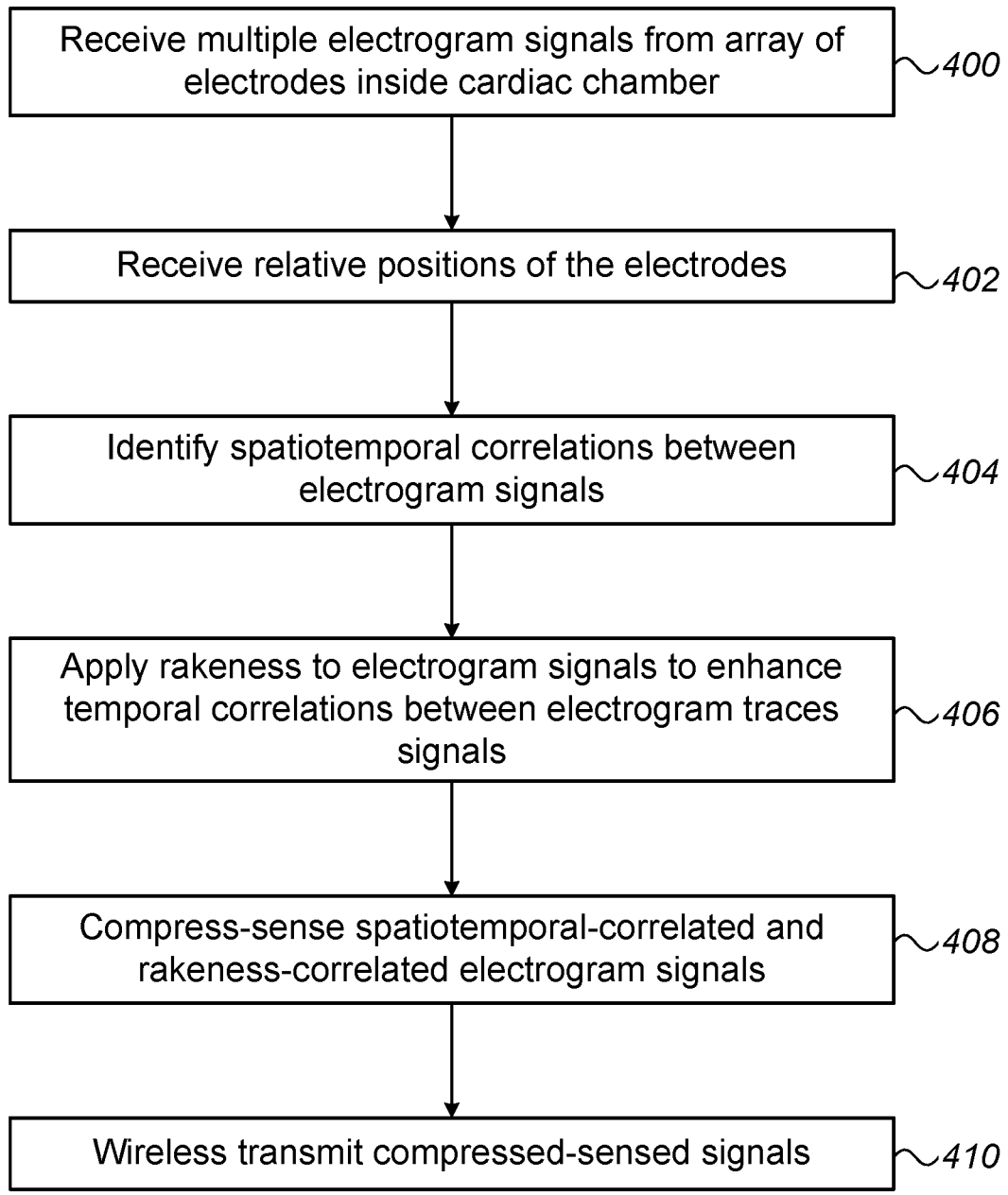
FIG. 4 is a flow chart that schematically describes a method for spatiotemporally-correlated and rakeness-processed compressed sensing (CS) of electrograms, in accordance with an embodiment of the present invention.

Compressed Sensing of
Spatiotemporally-Correlated and
Rakeness-Processed Multiple Electrograms FIG. 4 is a flow chart that schematically describes a method for spatiotemporally correlated and rakeness-processed compressed sensing (CS) of electrograms, in accordance with an exemplary embodiment of the present invention.

The algorithm, according to the presented exemplary embodiment, carries out a process that begins at a data receiving step 400, in which a data acquisition module, such as module 33 of FIG. 1, or module 110 of FIG. 3, receives multiple electrograms acquired by an electrode array, as described above.

The data acquisition module further receives locations of the electrodes at which the electrograms were acquired, at a receiving locations step 402. The locations are measured by any known method, such as by position tracking of a catheter, or by a prespecified map for an implant. The locations may be provided as relative positional relations (e.g., relative locations on a given grid). A processor, at least one of which, in the flow chart of FIG. 4, is assumed to be included among the data acquisition modules, performs all subsequent local processor-related steps using the received (e.g., uploaded as a table) locations, such as described in the following steps.

Next, at a spatiotemporal correlation identification step 404, each processor of a data acquisition module identifies electrograms that are spatiotemporally correlated based on their positions in the array (e.g., based on a relative distance between electrodes).

At a rakeness step 406, each processor of the data acquisition module applies rakeness to the electrograms. The motivation behind using rakeness is that, with real life signals, it is possible to reduce the reconstruction error $\|x-\hat{x}\|$ after the solution of Eq. 1 below by identifying second-order correlations between signals (e.g., electrograms).

Rakeness $\rho$ between two electrograms u and v can be defined as $\rho(u,v)=E_{u,v}[|(u,v)|^2]$, where $E_{u,v}$ refers to the expectation with respect to the two vectors and $\rho$ maximizes the signal energy for most correlated vectors. In this method, each signal $x_j$ is preprocessed by multiplying it with a different pseudo-random code (i.e., unique per signal $x_j$), comprising a sequence of "1", "0", and "−1". The code incorporates the input statistics and thus capitalizes on the correlation that exists (i.e., pseudo-random-code-imposed correlation) between the input signal and the code to identify correlation among electrograms and the pseudo-random code. In conclusion, in an exemplary embodiment, a processor reconstructs the input signal by using mixed-norm recovery algorithm which takes into account signals energies, so as to achieve better reconstruction performance (e.g., in SNR or CR senses). Details of the rakeness-based compressed sensing method can be found in "Rakeness in the Design of Analog-to-Information Conversion of Sparse and Localized Signals," by M. Mangia et al., IEEE TRANSACTIONS ON CIRCUITS AND SYSTEMS-I: REGULAR PAPERS, VOL. 59, NO. 5, May 2012.

After steps 404 and/or 406 are performed to identify spatiotemporal correlations between electrograms and to rakeness-process the electrograms, each processor of the data acquisition module performs compressed sensing on the electrograms, at a compressed sensing step 408, using either spatiotemporally-correlated electrograms identified as such (e.g., having a degree of correlation ranging above a pre-specified absolute value threshold, in that sense a maximal degree of correlation of +1 and −1 are considered both maximal) or both spatiotemporally-correlated electrograms and rakeness-processed electrograms. Gaining on steps 404 and/or 406, the processor can compress the multi-channel electrograms with higher CR without compromising quality of data subsequently reconstructed from the compressed data (e.g., without degrading an SNR of the reconstructed data).

CS based on spatiotemporal correlations is performed by minimizing the $\ell_{1,2}$ norm as described in brief below:

Consider a 2D array of L electrodes where the signal X is acquired from various channels with a sensing matrix $\Phi$ and the measurement matrix Y which can be described as $Y=\Phi X+n$, where n is the measurement noise, modeled as spatiotemporally white Gaussian noise. In the measurement vector, X, $X=[x_1, x_2, \ldots, x_L]$, each $x_j$ component is the time-dependent signal acquired from the j-th single electrode. Let also $A=[\alpha_1, \alpha_2, \ldots, \alpha_L]$ the matrix composed by the sparse representation vectors of $[x_1, x_2, \ldots, x_L]$, with $x_j=\psi\alpha_j$, j=1, 2, ... L, or, with a more compact notation, $X=\Psi A$. In matrix A, given that the signal x is K-sparse in an arbitrary basis $\Psi=[\psi_1, \psi_2, \ldots \psi_N]$ x can be represented as $x=\psi\alpha$, where $\alpha$ is an N-dimensional vector with only K<<N nonzero elements in the matrix $\Psi$. K and N are related by sparsity which is given by $(1-K/N)\cdot 100\%$.

From the compressed measurement samples, the signal can be reconstructed by solving the minimization problem given by $$\hat{\alpha}=\arg\arg\min_\alpha \|\alpha\|_1 \text{ subject to } y=\phi x+n=\Phi\psi\alpha, \qquad \text{Eq. 1}$$

where $\|\alpha\|_t$ is the $\ell_1$ norm of the signal. Further, the reconstructed input signal is given by $\hat{x}=\psi\hat{\alpha}$.

The multi-channel atrial electrograms share similarities among the adjacent channels, which can be exploited for an improved reconstruction performance. Multi-channel CS acquisition can be formulated as a multiple-measurement vector (MMV) problem and can be solved with jointly sparse recovery algorithms. The aim of MMV compressed sensing is to recover the jointly sparse A, which can be formulated as $$\hat{A}=\arg\arg\min_A \|A\|_{1,2} \text{ subject to } Y=\Phi\psi\alpha, \qquad \text{Eq. 2}$$

where the joint sparsity in A is induced by the $\ell_{1,2}$ mixed-norm defined by $\ell_{1,2}=\|A\|_{1,2}=(\Sigma_{j=1}^L(\Sigma_{i=1}^N|A_{i,j}|^2)^{1/2}$, meaning finding most correlated electrograms by minimizing the mixed-norm $\|A\|_{1,2}$. Details of the rakeness-based compressed sensing (rak-CS) method can be found in the aforementioned paper by M. Mangia et al., IEEE TRANSACTIONS ON CIRCUITS AND SYSTEMS-I: REGULAR PAPERS, VOL. 59, NO. 5, May 2012.

Finally, at a compressed sensing data transmission step 410, the compressed sensing EP data is wirelessly transmitted, for example, from a wearable data acquisition module to a base station.

Evaluated Performance of Spatiotemporally-Correlated and Rakeness-Processed Compressed Sensing The following sections compare SNR of reconstructed electrograms for the cases of (a) using rakeness vs. using standard CS, and (b) using mixed-norm $\ell_{1,2}$ vs. using $\ell_1$ norm. The SNR results were compared using same numbers of base functions (i.e., linear basis dimensions), meaning for same CR values.

In a demonstration of the disclosed techniques, atrial electrograms were recorded on the epicardium, the surface of the heart, using a 46 mm by 14 mm flexible multi-electrode array with 192 gold-plated electrodes and a 256-channel data-acquisition system. The data was acquired using analog front-end signal acquisition circuitry consisting of an amplifier with a gain of 60 dB, a bandpass filter with the bandwidth extending from 0.5 to 400 Hz, and an analog-to-digital converter with a resolution of 16 bits, which sampled the analog signal at 1 kHz. A total of 10 electrode-array sections were required to cover the entire surface area of the atria. For rakeness-based CS (rak-CS), one of the recorded sections was used as a reference for the correlation matrix estimation.

Using an $\ell_1$ norm, a compressed sensing code decodes and reconstructs the signals by solving Eqs. 1 and 2, using a wavelet transformation basis. The reconstructed signal is compared to the original signal using the performance metric, reconstruction signal-to-noise ratio (RSNR) given by $$RSNR_{dB} = 20\log\left(\frac{\|x\|}{\|x-\hat{x}\|}\right) \qquad \text{Eq. 3}$$

The reconstruction performance, i.e., the average RSNR (ARSNR) as a function of CR, of a standard compressed sensing (CS) method that minimizes only the $\ell_1$ norm without preferred choice of electrograms, is compared with reconstruction performance of mixed-norm $\ell_{1,2}$ compressed sensing recovery approach (the aforementioned MMV) that minimizes the $\ell_1$ norm for spatiotemporally-correlated electrograms.

Figure 5A:
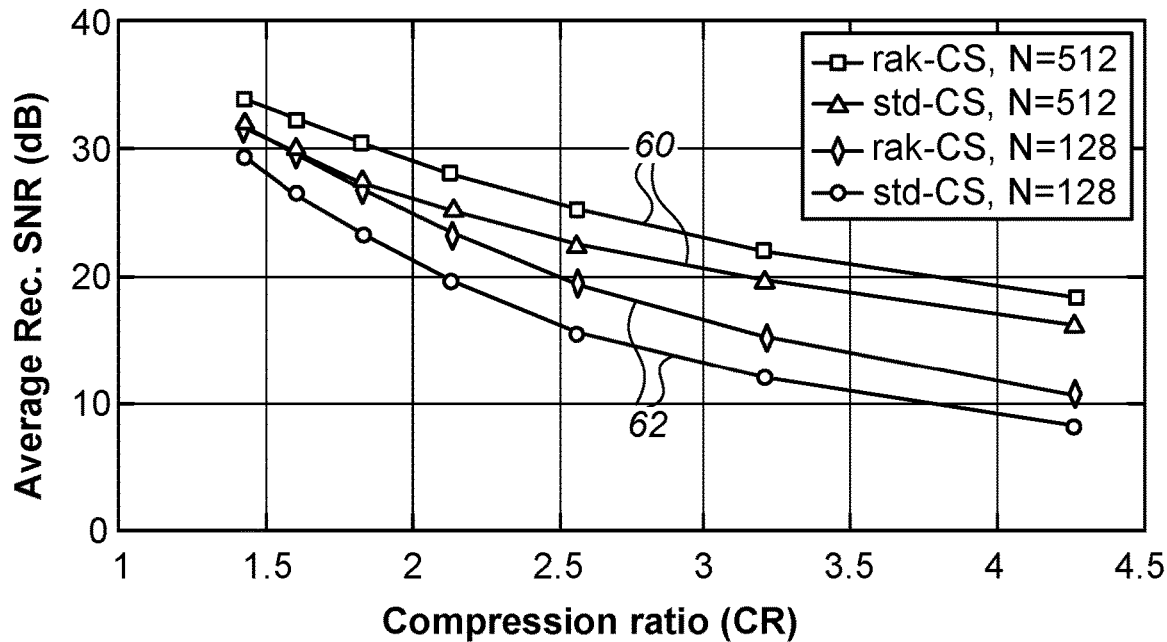
FIGS. 5A and 5B are graphs of spatial-domain and time-domain average reconstructed SNR (ARSNR) of electrogram signals as a function of compression ratio (CR) for compressed sensing (CS) signals both with and without rakeness, in accordance with exemplary embodiments of the present invention.
Figure 5B:
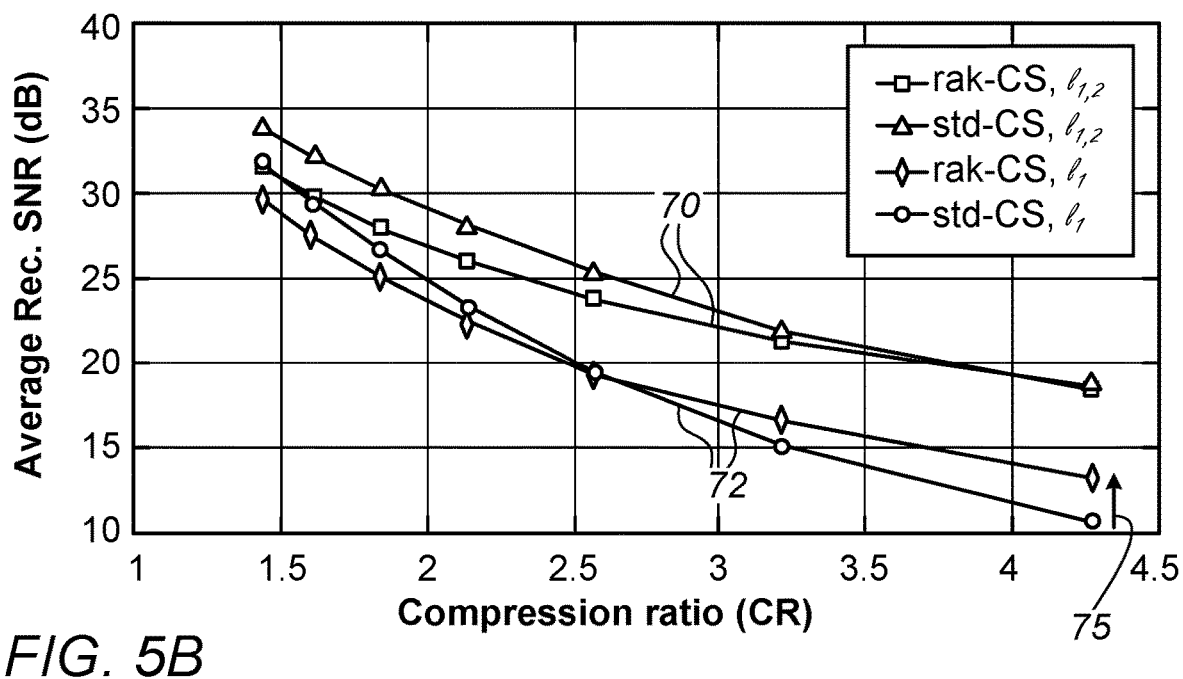

FIGS. 5A and 5B are graphs of spatial-domain and time-domain average reconstructed SNR of (ARSNR) of electrogram signals as a function of CR for signals with compressed sensing (CS) both with and without rakeness, in accordance with embodiments of the present invention.

FIGS. 5A and 5B show two CS approaches, standard CS (62) and rak-CS (60) on a data set, composed of real medical recordings. The performance of rak-CS (60) is better than standard CS (62), especially at higher compression ratios. In particular, the difference in the achieved ARSNR in rak-CS and standard CS, for CR=4.26, in the time domain, is 7.7 dB for AF waveforms.

In FIG. 5B, the multi-channel data is modeled as a multiple-measurement-vector problem and the mixed-norm is used to exploit the group structure of the signals in the spatial domain to obtain improved reconstruction performance (70) over $\ell_1$ norm minimization performance (72). Using the mixed-norm recovery approach, for CR=4.26, the difference in achieved ARSNR performance between rak-CS and standard CS is 5 dB for AF.

Moreover, without any use of rakeness, the $\ell_{1,2}$ mixed-norm recovery approach yields by itself, as FIG. 5B shows for CR=4.26, a 3.2 dB better ARSNR (75) than that achieved using $\ell_1$ norm. Therefore, providing the relative positions to use spatiotemporal correlations between the multiple electrogram signals enables the compressed sensing of the multiple electrogram signals with a given CR (e.g., 4.26), such that the compressed signals yield reconstructed signals having a superior SNR compared with a method not using the aforementioned spatiotemporal correlations presented by signals acquired using dense electrode grids.

Figure 6A:
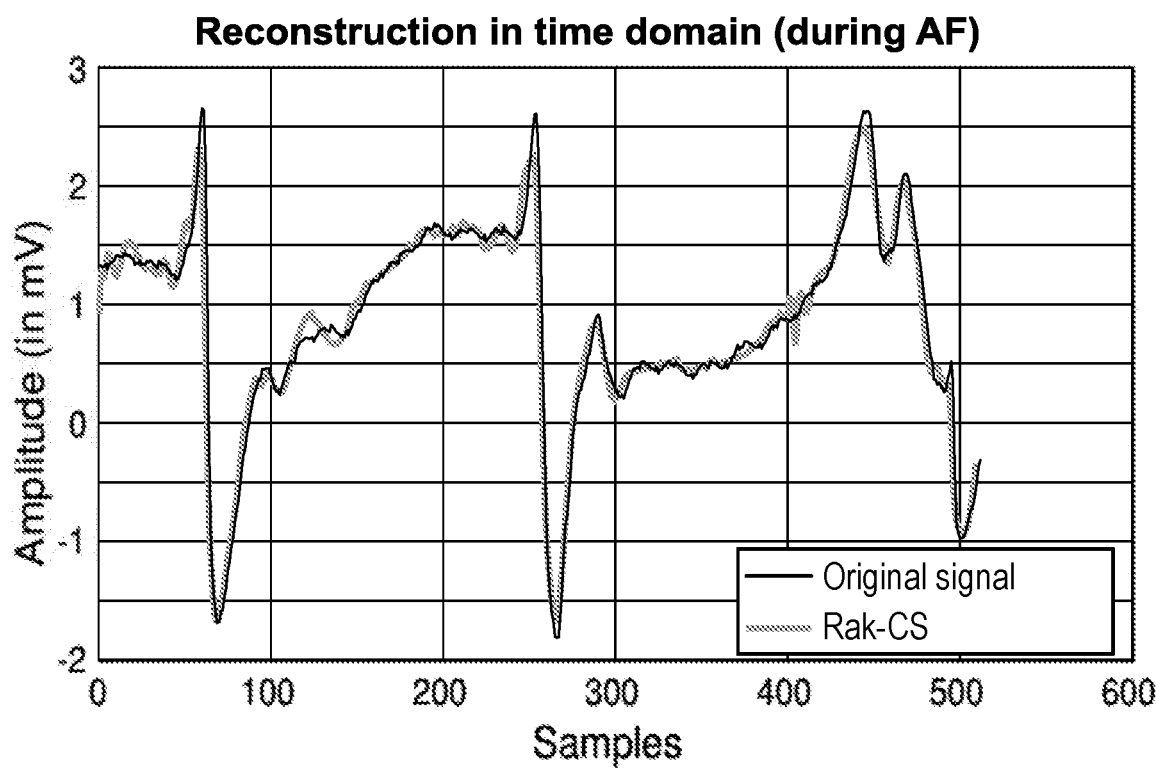
FIGS. 6A and 6B are graphs of spatial-domain and time-domain rakeness-based compressed sensing (rak-CS) signals after being reconstructed vs. the original recorded electrogram signals, in accordance with an exemplary embodiment of the present invention.
Figure 6B:
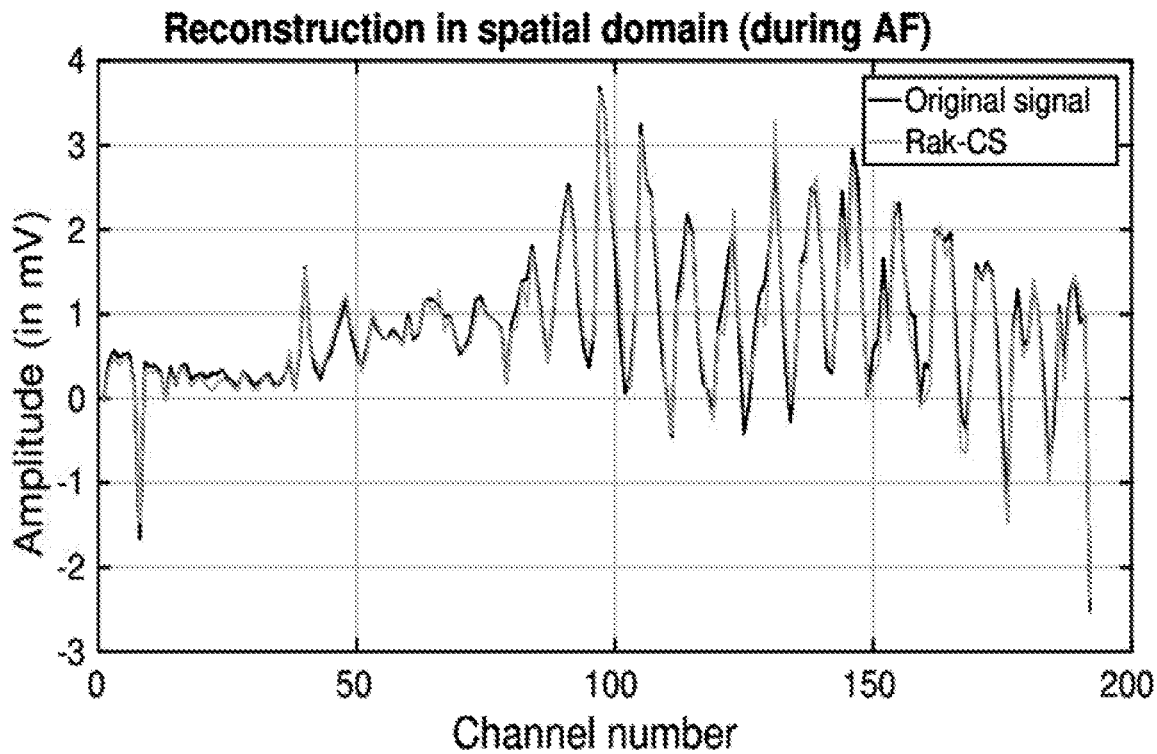

FIGS. 6A and 6B are graphs of spatial-domain and time-domain rakeness-based compressed-sensed (rak-CS) signals after being reconstructed vs. the original recorded electrogram signals, in accordance with an embodiment of the present invention. The reconstruction waveforms were low-pass filtered (up to 400 Hz), making the waveforms look less noisy and thus easier to analyze by a physician.

FIG. 6A shows the reconstruction of the atrial electrograms in the time domain during AF for an arbitrarily selected channel number (ch=90) out of 512 recorded channels. FIG. 6B shows the reconstruction of the AEGs in the spatial domain, during AF, for an arbitrarily chosen time instant. As seen, the rak-CS reconstruction of the signal adds high frequency noise in the time-domain. However, this noise does not distort the signal and can be largely removed by standard signal processing methods.

Hardware Implementation of Rakeness

In parallel to algorithmic tools, embodiments of the present invention offer data acquisition circuitry configured for energy savings, which is highly important in implant-wearable devices, such as wearable data acquisition and wireless transmission module 110.

Figure 7:
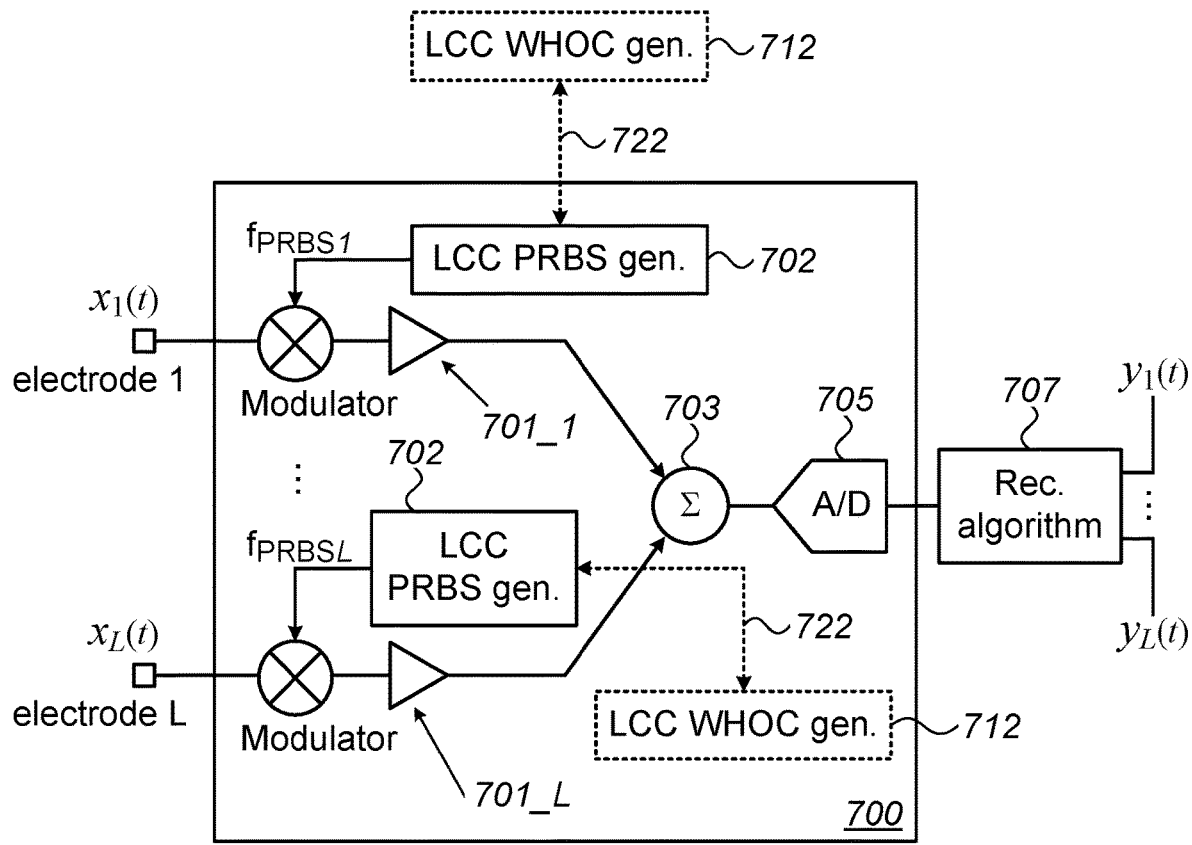
FIG. 7 is a block diagram of a multi-channel rakeness data acquisition circuitry, for use with an analog acquisition front end, that employs a single analog-to-digital convertor (ADC), in accordance with exemplary embodiments of the present invention.

FIG. 7 is a block diagram of a multi-channel rakeness data acquisition circuitry 700 for use with an analog acquisition front end that employs a single analog-to-digital convertor (ADC) 705, in accordance with exemplary embodiments of the present invention. In one exemplary embodiment, acquisition circuitry 700 is comprised in data acquisition module 33 of system 20 of FIG. 1. In another exemplary embodiment, acquisition circuitry 700 is comprised in wearable data acquisition and wireless transmission module 110 of FIG. 3.

In FIG. 7, each of the L electrograms $X_1, x_2, \ldots x_L$ (acquired by electrodes 1, 2, ... L) is preprocessed in respective front-end circuitries 701_1, 701_2, ... 701_L, by multiplying the electrogram with a pseudo-random code, comprising a sequence in time of "1", "0", and "−1" using a low-cross-correlation (LCC) PRBS generator 702 to generate the "1", "0", and "−1" signals (e.g., sequences) having low cross-correlation.

Alternatively (722), a Walsh-Hadamard orthogonal coding can be applied to the analog signals, by using instead of LCC-PRBS generator 702, an LCC Walsh-Hadamard orthogonal coding (LCC WHOC) generator 712. Using generator 712 ensures very low cross-correlation between the channels and also suppresses 1/f noise and offset.

The rakeness-processed (e.g., rakeness-coded) electrograms are first summed by an adder 703 and only then inputted into a single analog-to-digital convertor (ADC) 705, thereby saving one energy-costly ADC element per channel (i.e., reducing the number of ADC elements from L>>1 to one).

A recording algorithm 707, such as may be used by processor 28 of system 20, or by signal reconstruction unit 52 of base station 111 of FIG. 3, recovers the compressed sensing signal.

Signal reconstruction unit 52 can perform the reconstruction of the pseudorandom codes that are different per channel. While having the same energy spectrum and the same length, each pseudorandom code (e.g., fPBRS$_j$) modulates a respective channel signal (e.g., X$_j$) by a different sequence of 1, −1 and 0. Using the known sensing matrix Φ, the basis in which the signal is sparse, Ψ, and the measurements "y(t)" (i.e., the output signals in FIGS. 7, 8A, and 8B), a processor estimates the aforementioned vector α. With α estimated the processor can reconstruct the original vector signal "x(t)" (i.e., the input analog signals in FIGS. 7, 8A, and 8B).

The circuitry shown in FIG. 7 is shown in a simplified manner, for clarity of presentation. Possible implementation details, such as given in FIGS. 8A and 8B, are thus omitted from FIG. 7.

Figure 8A:
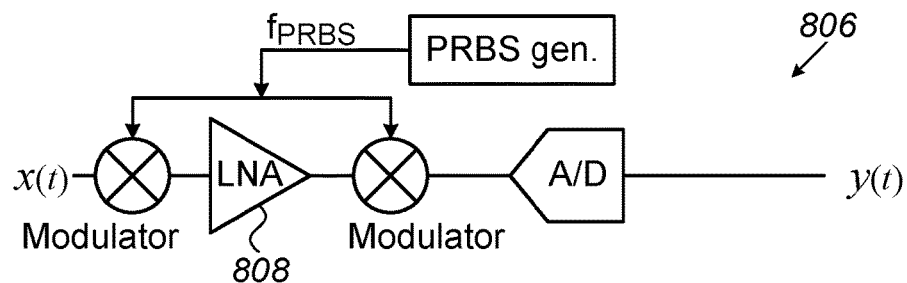
FIGS. 8A and 8B are block diagrams of data acquisition circuitries using rakeness to suppress 1/f noise and offset, and compressed sensing (FIG. 8B only), in accordance with exemplary embodiments of the present invention.
Figure 8B:
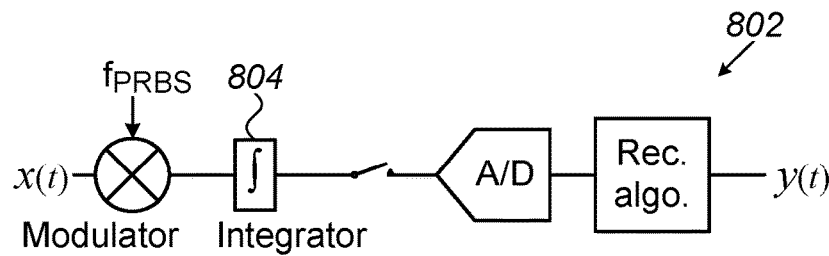

FIGS. 8A and 8B are block diagrams of data acquisition circuitries 806 and 802 using rakeness to suppress 1/f noise and offset, and compressed sensing (FIG. 8B only), in accordance with embodiments of the present invention.

FIG. 8A shows circuitry 806 used in FIG. 7, in which a low noise amplifier (LNA) 808 is preceded by a modulator to suppress the amplifier's 1/f noise and offset contribution. The technique used herein is spread-spectrum modulation. Since the input signal is spread over a larger bandwidth, the transmission is more secure and is also protected from interfering signals (e.g., 50/60 Hz). At the output of LNA 808, the signals are demodulated using the same PRBS sequence to obtain the amplified input signal.

FIG. 8B shows circuitry 802 used in FIG. 7, in which a modulator is preceding a CS front-end to not only apply rakeness but also benefit from suppression of the integrating amplifier's 804 1/f noise and offset.

Although the embodiments described herein mainly address compressed-sensing electrophysiological data, the methods and systems described herein can also be used in other applications, such as with CS of other forms of non-stationary data, such as originating from (bio-) sensors or in-vitro electrophysiological analysis, such as signals originating from cellular or molecular level (e.g., from a cell culture).

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
data acquisition circuitry configured to acquire multiple signals using multiple respective electrodes of an array of electrodes configured to be coupled to one of (i) an organ of a patient and (ii) tissue or cell culture; and
a processor, which is configured to:
identify spatiotemporal correlations between the multiple signals based upon relative distances between the electrodes;
hold a definition of a mixed-norm that is defined as a function of relative positions of the electrodes in the array; and
jointly compress the multiple signals based upon their identified spatiotemporal correlations in a compressed-sensing (CS) process that minimizes the mixed-norm.

2. The apparatus according to claim 1, wherein the signals are one of atrial electrograms and ventricular electrograms.

3. The apparatus according to claim 1, wherein the signals are electroencephalograms.

4. The apparatus according to claim 1, wherein the data acquisition circuitry is further configured to apply respective pseudo-random sequences to the signals so as to increase sparsity and incoherence of a measurement matrix $\Phi$, and wherein the processor is configured to minimize the mixed-norm for the measurement matrix $\Phi$ having the increased sparsity and incoherence.

5. The apparatus according to claim 4, wherein the data acquisition circuitry comprises a pseudo-random binary noise (PRBS) generator for generating the pseudo-random sequences.

6. The apparatus according to claim 4, wherein the data acquisition circuitry comprises a Walsh-Hadamard orthogonal coding (WHOC) generator for generating the pseudo-random sequences.

7. The apparatus according to claim 1, wherein, the data acquisition circuitry is further configured to spectrally spread the input signal.

8. The apparatus according to claim 1, wherein the data acquisition circuitry comprises a single analog-to-digital convertor (ADC) configured to convert the multiple signals into digital signals.

9. The apparatus according to claim 1, and comprising a wireless unit configured to transmit the compressed signals to a base station.

10. The apparatus according to claim 1, and comprising a wearable package containing the data acquisition circuitry and the processor.

11. An apparatus, comprising:
data acquisition circuitry configured to acquire multiple signals using multiple respective electrodes of an array of electrodes coupled to one of (i) an organ of a patient and (ii) tissue or cell culture, the data acquisition circuitry comprising a pseudo-random bit sequence generator and a modulator, the pseudo-random bit sequence generator configured to drive the modulator, thereby simultaneously acquiring the signals and suppressing flicker noise of a front-end of the signal acquisition circuitry; and
a processor, which is configured to:
identify spatiotemporal correlations between the multiple signals based upon relative distances between the electrodes;
hold a definition of a mixed-norm that is defined as a function of relative positions of the electrodes in the array;
jointly compress the multiple signals in a spatial domain and in a time domain based upon the identified spatiotemporal correlations of the multiple signals; and
reconstruct the multiple signals using the mixed-norm in a recovery algorithm which takes into account signals energies.

12. A method, comprising:
acquiring multiple signals using multiple respective electrodes of an array of electrodes configured to be coupled to one of (i) an organ of a patient and (ii) tissue or cell culture;
identifying spatiotemporal correlations between the multiple signals based upon relative distances between the electrodes;
holding a definition of a mixed-norm that is defined as a function of relative positions of the electrodes in the array; and
jointly compressing the multiple signals based upon their identified spatiotemporal correlations in a compressed-sensing (CS) process that minimizes the mixed-norm.

13. The method according to claim 12, wherein the signals are one of atrial electrograms and ventricular electrograms.

14. The method according to claim 12, wherein the signals are electroencephalograms.

15. The method according to claim 12, and comprising applying respective pseudo-random sequences to the signals so as to increase sparsity and incoherence of a measurement matrix $\Phi$, wherein jointly compressing the multiple signals comprises minimizing the mixed-norm for the measurement matrix $\Phi$ having the increased sparsity and incoherence.

16. The method according to claim 15, wherein the pseudo-random sequences comprise pseudo-random binary noise (PRBS) sequences for generating the pseudo-random sequences.

17. The method according to claim 15, wherein the pseudo-random sequences comprise Walsh-Hadamard orthogonal coding (WHOC) sequences for generating the pseudo- random sequences.

18. The method according to claim 12, and comprising spectrally spreading the input signal.

19. The method according to claim 12, wherein acquiring the multiple signals comprises converting the multiple signals into digital signals using a single analog-to-digital convertor (ADC).

20. The method according to claim 12, and comprising wirelessly transmitting the compressed signals to a base station.

21. The method according to claim 12, wherein acquiring and jointly compressing the multiple signals comprises wearing a device configured for acquiring and jointly compressing multiple signals.

\* \* \* \* \*